United States Patent
Arava et al.

(10) Patent No.: US 10,947,191 B2
(45) Date of Patent: Mar. 16, 2021

(54) PROCESS FOR THE PREPARATION OF GLYCOPYRROLATE TOSYLATE

(71) Applicant: SOL-GEL TECHNOLOGIES LTD., Ness Ziona (IL)

(72) Inventors: Veera Reddy Arava, Hyderabad (IN); Madhusudhanarao Rayapureddi, Hyderabad (IN); Venkateswarlu Jasti, Hyderabad (IN)

(73) Assignee: Sol-Gel Technologies Ltd., Ness Ziona (IL)

( * ) Notice: Subject to any disclaimer, the term of this patent is extended or adjusted under 35 U.S.C. 154(b) by 0 days.

(21) Appl. No.: 16/633,263

(22) PCT Filed: Jul. 26, 2018

(86) PCT No.: PCT/IL2018/050838
§ 371 (c)(1),
(2) Date: Jan. 23, 2020

(87) PCT Pub. No.: WO2019/021290
PCT Pub. Date: Jan. 31, 2019

(65) Prior Publication Data
US 2020/0377456 A1    Dec. 3, 2020

Related U.S. Application Data

(60) Provisional application No. 62/537,510, filed on Jul. 27, 2017.

(51) Int. Cl.
*C07D 207/12* (2006.01)
*C07C 309/30* (2006.01)

(52) U.S. Cl.
CPC .......... *C07D 207/12* (2013.01); *C07C 309/30* (2013.01)

(58) Field of Classification Search
CPC .......................... C07D 207/12; C07C 309/30
See application file for complete search history.

(56) References Cited

U.S. PATENT DOCUMENTS

| 7,915,303 B2 | 3/2011 | Baxter |
| 9,006,461 B2 | 4/2015 | Statler et al. |
| 2016/0052879 A1 | 2/2016 | Shaw et al. |

FOREIGN PATENT DOCUMENTS

WO    WO-2010115937 A1    10/2010

OTHER PUBLICATIONS

International Search Report and Written Opinion dated Oct. 23, 2018 issued in PCT International Application No. PCT/IL2018/050836, dated Jul. 26, 2018.
Tang, R. R., & Gong, N. H. (2009). The Rapid and Efficient Synthesis of Bromohydrins from Olefins under HBr/$H_2O_2$ System by Visible Light Induced. *Bulletin of the Korean Chemical Society*, 30(8), 1832-1834.

*Primary Examiner* — Karen Cheng
(74) *Attorney, Agent, or Firm* — Mark S. Cohen; Pearl Cohen; Zedek Latzer Baratz LLP

(57) ABSTRACT

This invention is directed to a process for the preparation of glycopyrrolate tosylate comprising the step of reacting a halogen salt of glycopyrrolate with tosylic acid or a salt thereof in the presence of hydrogen peroxide and at least one unsaturated organic agent.

14 Claims, No Drawings

PROCESS FOR THE PREPARATION OF GLYCOPYRROLATE TOSYLATE

CROSS REFERENCE TO RELATED APPLICATIONS

This application is a National Phase Application of PCT International Application No. PCT/IL2018/050838, International Filing Date Jul. 26, 2018, which claims the benefit of U.S. Provisional Application 62/537,510 filed Jul. 27, 2017, which is hereby incorporated by reference.

FIELD OF THE INVENTION

This invention is directed to a process for the preparation of glycopyrrolate tosylate.

BACKGROUND OF THE INVENTION

Glycopyrronium tosylate, also known as (1,1-dimethylpyrrolidin-1-ium-3-yl) 2-cyclopentyl-2-hydroxy-2-phenylacetate; 4-methylbenzenesulfonate or glycopyrrolate tosylate, is an anti-muscarinic agent. Other glycopyrrolate salts are used as antiasthmatic or antispasmodic agents administered either intravenously, orally or topically in accordance with the medical indication. Glycopyrronium bromide and glycopyrronium tosylate have been clinically tested for the topical treatment of hyperhidrosis.

Glycopyrrolate tosylate has the following chemical structure:

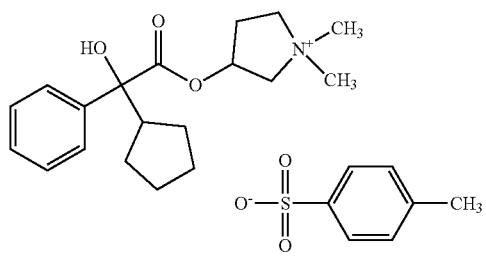 [SMILES: C[N+]1(C)CCC(OC(=O)C(O)(c2ccccc2)C2CCCC2)C1 ; Cc1ccc(S(=O)(=O)[O-])cc1]

Several syntheses of glycopyrrolate tosylate have been disclosed, one of which is the conversion of the glycopyrrolate bromide (commercially available as "glycopyrrolate") into the tosylate. However, these syntheses have been prone to give rise to high levels of by-products, which are highly undesirable and require further purification processes. Typical syntheses of the glycopyrrolate tosylate have been disclosed in the following patent documents: U.S. Pat. No. 9,006,461, WO 2010/115937 and U.S. Pat. No. 7,915,303.

Acknowledgement of the above references herein is not to be inferred as meaning that these are in any way relevant to the patentability of the presently disclosed subject matter.

There is therefore a need for an efficient and straightforward process for the preparation of glycopyrrolate tosylate from the halogen salt of glycopyrrolate that affords a final product having lower amounts of halide content (starting material).

SUMMARY OF THE INVENTION

The present invention provides a process for the preparation of glycopyrrolate tosylate comprising the step of reacting a halogen salt of glycopyrrolate with tosylic acid or a salt thereof in the presence of hydrogen peroxide and at least one unsaturated organic agent.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, this invention provides a process for the preparation of glycopyrrolate tosylate comprising the step of reacting a halogen salt of glycopyrrolate with tosylic acid or a salt thereof in the presence of hydrogen peroxide and at least one unsaturated organic agent.

The process of this invention is described in Scheme 1:

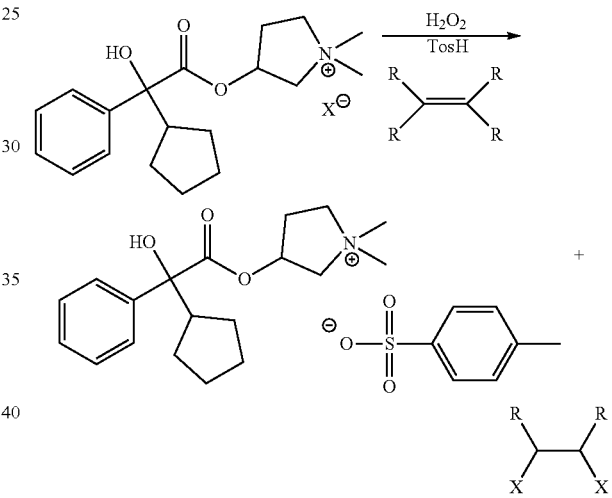

wherein:

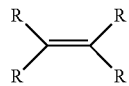

is a halide anion;

$$\underset{R}{\overset{R}{>}}=\underset{R}{\overset{R}{<}}$$

is an unsaturated organic agent as described herein;

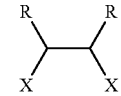

is an addition product of $X_2$ (see formation of $X_2$ in Scheme 2) to the unsaturated bond; and
TsOH is tosylic acid.
Scheme 1: Synthetic Scheme for the Preparation of Glycopyrrolate Tosylate.

In the process described in Scheme 1, the halide anion oxidizes to a $X_2$ halogen and in the presence of acid the $X_2$ halogen reacts with the unsaturated bond, as described in Scheme 2:

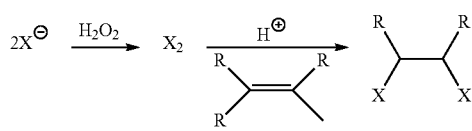

Scheme 2: A Parallel Synthetic Scheme Occurring in Parallel to the Glycopyrrolate Tosylate Reaction of this Invention.

The process of this invention provides a product having less than 2% halide content.

When referring to "halogen salt of glycopyrrolate" it should be understood to encompass a salt of the glycopyrrolate cation (a pynolydinium cation) with a corresponding halogen anion (e.g. $I^-$, $Cl^-$, $Br^-$, $F^-$).

When referring to "tosylic acid" it should be understood to encompass a compound having the formula (p-toluenesulfonic acid):

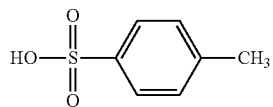

Tosylic acid may also include a salt of said acid relating to the corresponding anionic base and a counter cation.

The term "unsaturated organic agent" should be understood to include at least one organic substance in the comprising at least one unsaturated bond (e.g. double bond, triple bond). In other embodiments the unsaturated organic agent is substituted or unsubstituted alkene, alkyne, cycloalkene, cycloalkyne, heterocycle, or aryl.

In some embodiments, said at least one unsaturated organic agent is selected from cyclopentene, butene, pentene, cyclohexene, styrene, phenol and any combinations thereof.

In some embodiments, the process of the present invention is performed in the presence of a mixture of at least one saturated organic agent and at least one unsaturated organic agent.

The term "saturated organic agent" should be understood to include at least one organic substance wherein all its bonds are single sigma bonds.

In other embodiments the saturated organic agent is substituted or unsubstituted alkane, cycloalkane or a heterocycle.

In other embodiments, said at least one saturated organic agent is selected from cyclohexane, n-hexane, dichloromethane (DCM), heptane, and any combinations thereof.

As used herein, the term "alkane" can be any straight- or branched-chain alkane group containing up to about 30 carbons. In various embodiments, an alkane includes $C_1$-$C_5$ carbons. In some embodiments, an alkane includes $C_1$-$C_6$ carbons. In some embodiments, an alkane includes $C_1$-$C_8$ carbons. In some embodiments, an alkane includes $C_1$-$C_{10}$ carbons. In some embodiments, an alkane is a $C_1$-$C_{12}$ carbons. In some embodiments, an alkane is a $C_1$-$C_{20}$ carbons. In some embodiments, branched alkane is an alkane substituted by alkyl side chains of 1 to 5 carbons. In various embodiments, the alkane may be unsubstituted. In some embodiments, the alkane may be substituted by a halogen, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl.

The term "alkene" as used herein refers to an alkane as described above having at least one double bond. In various embodiments, an alkene includes $C_2$-$C_5$ carbons. In some embodiments, an alkene includes $C_2$-$C_6$ carbons. In some embodiments, an alkene includes $C_2$-$C_8$ carbons. In some embodiments, an alkene includes $C_2$-$C_{10}$ carbons. In some embodiments, an alkene is a $C_2$-$C_{12}$ carbons. In some embodiments, an alkene is a $C_2$-$C_{20}$ carbons. In another embodiment, the alkene may be substituted by alkyl, halogen, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl.

The term "alkyne" as used herein refers to an alkane as described above having at least one triple bond. In various embodiments, an alkyne includes $C_2$-$C_5$ carbons. In some embodiments, an alkyne includes $C_2$-$C_6$ carbons. In some embodiments, an alkyne includes $C_2$-$C_8$ carbons. In some embodiments, an alkyne includes $C_2$-$C_{10}$ carbons. In some embodiments, an alkyne is a $C_2$-$C_{12}$ carbons. In some embodiments, an alkyne is a $C_2$-$C_{20}$ carbons. In another embodiment, the alkyne may be substituted by alkyl, halogen, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl.

As used herein, the term "arene" refers to any aromatic ring that can be either substituted or unsubstituted. The arene can be a sole substituent, or the aryl group can be a component of a larger substituent, such as in an arylalkyl, arylamino, arylamido, etc. Exemplary arene groups include, without limitation, phenyl, tolyl, xylyl, furanyl, naphthyl, pyridinyl, pyrimidinyl, pyridazinyl, pyrazinyl, triazinyl, thiazolyl, oxazolyl, isooxazolyl, pyrazolyl, imidazolyl, thiophene-yl, pyrrolyl, phenylmethyl, phenylethyl, phenylamino, phenylamido, etc. Substitutions include but are not limited to: F, Cl, Br, I, $C_1$-$C_5$ linear or branched alkyl, $C_1$-$C_5$ linear or branched haloalkyl, $C_1$-$C_5$ linear or branched alkoxy, $C_1$-$C_5$ linear or branched haloalkoxy, $CF_3$, CN, $NO_2$, $-CH_2CN$, $NH_2$, NH-alkyl, N(alkyl)$_2$, hydroxyl, $-OC(O)$ $CF_3$, $-OCH_2Ph$, $-NHCO$-alkyl, COOH, $-C(O)Ph$, $C(O)$ O-alkyl, $C(O)H$, or $-C(O)NH_2$.

A "heterocycle" refers, in various embodiments, to a ring structure comprising in addition to carbon atoms, sulfur, oxygen, nitrogen or any combination thereof, as part of the ring. In some embodiment, the heterocycle is saturated or unsaturated. In some embodiments the heterocycle is a 3-10 membered ring. In some embodiments the heterocycle is a 3-12 membered ring. In some embodiments the heterocycle is a 6 membered ring. In some embodiments the heterocycle is a 5-7 membered ring. In some embodiments the heterocycle is a 3-8 membered ring. In some embodiments, the heterocycle may be unsubstituted or substituted by a halogen, alkyl, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In some embodiments, the heterocycle ring may be fused to another saturated or unsaturated cycloalkyl or heterocyclic 3-8 membered ring. In some embodiments, the heterocyclic ring is a saturated ring. In some embodiments, the heterocyclic ring is an unsaturated ring. Non limiting examples of a heterocycles include pyridine, piperidine, morpholine, piperazine, thiophene, pyrrole, benzodioxole, or indole.

The term "cycloalkane" refers, in various embodiments, to a ring structure comprising in carbon atoms, wherein the ring is saturated. The term "cycloalkene" refers, in various embodiments, to a ring structure comprising in carbon atoms and at least one double bond. The term "cycloalkyne" refers, in various embodiments, to a ring structure comprising in carbon atoms and at least one triple bond. In some embodiment, the cycloalkane, cycloalkene or cycloalkyne is a 3-10 membered ring. In some embodiments the cycloalkane, cycloalkene or cycloalkyne is a 3-12 membered ring. In some embodiments the cycloalkane, cycloalkene or cycloalkyne is a 6 membered ring. In some embodiments the cycloalkane, cycloalkene or cycloalkyne is a 5-7 membered ring. In some embodiments the cycloalkane, cycloalkene or cycloalkyne is a 3-8 membered ring. In some embodiments, the cycloalkane, cycloalkene or cycloalkyne may be unsubstituted or substituted by a halogen, alkyl, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In some embodiments, the cycloalkane, cycloalkene or cycloalkyne may be fused to another saturated or unsaturated 3-8 membered ring.

The term "in the presence of . . . " should be understood to define that the reaction between said halogen salt of glycopyrrolate and said tosylic acid or a salt thereof is performed when hydrogen peroxide and at least one unsaturated organic agent are present.

In some embodiments, said halogen salt of glycopyrrolate is mixed with said at least one unsaturated organic agent prior to addition of said hydrogen peroxide.

In other embodiments, said halogen salt of glycopyrrolate is mixed with said tosylic acid or salt thereof prior to addition of said hydrogen peroxide.

In some embodiments, said halogen salt of glycopyrrolate is mixed with said tosylic acid or salt thereof and said at least one unsaturated organic agent prior to addition of said hydrogen peroxide.

In some further embodiments, said halogen salt of glycopyrrolate is mixed with said at least one unsaturated organic agent prior to reacting with said tosylic acid or salt thereof.

In some embodiments, said hydrogen peroxide is added prior to or during said reaction of said halogen salt of glycopyrrolate and said tosylic acid or salt thereof.

In further embodiments, said halogen salt of glycopyrrolate is a bromide salt thereof.

In some embodiments, said tosylic acid or a salt thereof is p-toluene sulfonic acid monohydrate.

In some embodiments, the process of the invention provides a product having a less than 2% halide content. In some other embodiments, the process of the invention provides a product having less than 1% halide content. In further embodiments, the process of the invention provides a product having less than 0.5% halide content.

The term "halide content" of a product of a process of the invention should be understood to relate to the measured percentage of a halide (e.g. chloride, bromide etc.) in the product of the process of the invention. In another embodiment a halide content refers to the mole percentage of the halide in the product. This parameter, particularly the bromide ion, is typically measured by High Performance Liquid Chromatography (HPLC).

In some embodiments, the concentration of hydrogen peroxide used in the process of the invention is at least 10%. In other embodiments, the concentration of hydrogen peroxide used in the process of the invention is at least 30%. In some embodiments, the concentration of hydrogen peroxide used in the process of the invention is at least 40%.

In some embodiments, the molar ratio between the glycopyrrolate halide and the tosylic acid and the unsaturated organic agent is between 1:1:1 to 1:1:1.5 respectively.

In one embodiment, the term "about", refers to a deviance of between 0.0001-5% from the indicated number or range of numbers. In one embodiment, the term "about", refers to a deviance of between 1-10% from the indicated number or range of numbers.

The following examples are presented in order to more fully illustrate the preferred embodiments of the invention. They should in no way, however, be construed as limiting the broad scope of the invention.

EXAMPLES

Example 1. Preparation of Glycopyrrolate Tosylate with Cyclohexene as an Unsaturated Organic Agent

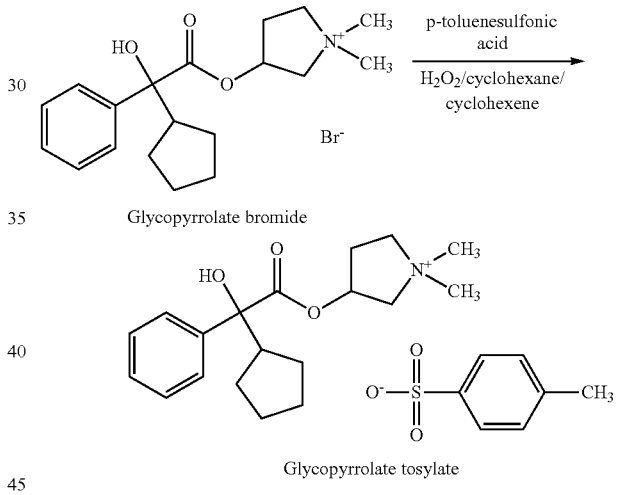

To the mixture of glycopyrrolate bromide pure threo isomer (50 g, 0.13 mole), cyclohexene (12.66 g; 0.15 mole), cyclohexane (230 ml) and p-toluene sulfonic acid monohydrate (23.89 g, 0.13 mole), 5.0 g (0.063 mole) of 42% hydrogen peroxide were added slowly at temperature 25-30° C. The obtained clear solution was stirred for 12 h at 23-30° C., and precipitation was observed. The solid was isolated by filtration to obtain 72 g of wet glycopyrrolate tosylate with unreacted glycopyrrolate bromide content of 0.11%. The solid was dissolved in water (210 ml) at 50-55° C., cooled to 0-5° C. and then isolated by filtration to give 71 g having 100% purity by HPLC. The solid was further dissolved in dichloromethane (320 ml) at 30-35° C. After removal of 90% (~470 ml) of dichloromethane under reduced pressure, cyclohexane (210 ml) was added. The mixture was cooled to 0-5° C. and filtered (51 g) and dried atmospherically to afford 42.5 g (0.0837 mole, 66.7% yield) of glycopyrrolate tosylate, purity by HPLC—100%. IR (KBr): 683.91-907.29 $cm^{-1}$ (C—H arom); 1013.29-1037.39 $cm^{-1}$ (C—N, C—O, C=S str); 1198.94 $cm^{-1}$ (C—O ester str); 1328.86, 1360.77, 1446.62 $cm^{-1}$ (S=O); 1736.86 $cm^{-1}$ (C=O ester); 2868.87-3032.36 cm$^{-1}$ (C—H aliph); 3429.2, 3573.95 cm$^{-1}$ (O—H str). ESI-MS(+): m/z=318.1 (glycopyrronium). $^1$H NMR (DMSO-d6): δ=1.18-1.23 (m, 2H), 1.38 (m, 1H), 1.49-1.61 (m, 5H), 2.05 (m, 1H), 2.28 (s, 3H), 2.61 (m, 1H), 2.91 (m, 1H), 3.07 (s, 3H), 3.14 (s, 3H), 3.48-3.51 (m, 1H), 3.57-3.60 (d, 1H), 3.66-3.67 (m, 1H), 3.81-3.83 (dd, 1H), 5.36 (m, 1H), 5.84 (s, 1H), 7.11-7.12 (d, 2H), 7.24-7.28 (t, 1H), 7.33-7.36 (t, 2H), 7.47-7.49 (d, 2H), 7.57-7.59 (d, 2H). DSC: a peak at 120.44° C.

X-ray diffraction: Characteristic peaks to identify Form—D is at diffraction angle 6.9, 10.3, 12.6, 13.7, 14.9, 15.3, 15.7, 16.4, 17.7, 18.2 or 20.6° 2φ.

TABLE 1

XRD data of glycopyrrolate tosylate prepared according to the present invention and of glycopyrrolate tosylate disclosed in U.S. Pat. No. 9,006,461

| Diffraction Angle (2φ) | INTENSITY (%) | |
|---|---|---|
| | Glycoryrrolate tosylate as disclosed in U.S. Pat. No. 9,006,461 | Glycopyrrolate tosylate prepared according to the process of the present invention |
| 6.87 ± 0.20 | 100 | 100 |
| 10.26 ± 0.20 | 19 | 8 |
| 12.55 ± 0.20 | 85 | 55 |
| 13.72 ± 0.20 | 15 | 20 |
| 14.91 ± 0.20 | 29 | 42 |
| 15.31 ± 0.20 | 18 | 27 |
| 15.68 ± 0.20 | 17 | 26 |
| 16.43 ± 0.20 | 14 | 21 |
| 17.73 ± 0.20 | 19 | 21 |
| 18.15 ± 0.20 | 25 | 34 |
| 18.60 ± 0.20 | 53 | 69 |
| 18.82 ± 0.20 | 28 | 55 |
| 19.59 ± 0.20 | 16 | 20 |
| 20.21 ± 0.20 | 26 | 34 |
| 20.62 ± 0.20 | 63 | 44 |
| 21.09 ± 0.20 | 19 | 22 |
| 21.63 ± 0.20 | 19 | 12 |
| 23.50 ± 0.20 | 14 | 16 |
| 25.15 ± 0.20 | 27 | 34 |

The glycopyrrolate tosylate prepared according to the method of the present invention has characteristic peaks of Form D, thus it can be considered as Form D.

Example 2. Preparation of Glycopyrrolate Tosylate with Cyclohexene as an Unsaturated Organic Agent, but without Crystallization in Dichloromethane To a mixture of glycopyrrolate bromide pure threo isomer (10 g, 0.025 mole), cyclohexene (2.53 g, 0.031 mole), cyclohexane (46 ml) and p-toluene sulfonic acid monohydrate (4.77 g, 0.025 mole), 1.0 g (0.013 mole) of 42% hydrogen peroxide was added slowly at temperature 25-30° C. The obtained clear solution was stirred at 25-30° C. for 12 h and precipitation was observed. The solid was isolated by filtration to obtain 15 g wet material with un-reacted glycopyrrolate bromide content of 0.25%. The solid was dissolved in water (36 ml) at 50-55° C., cooled to 0-5° C. and then isolated by filtration to give 13 g and further dried atmospherically to afford 8.8 g (0.017 mole, yield 69.2%) of glycopyrrolate tosylate, purity by HPLC—100%.

Example 3. Preparation of Glycopyrrolate Tosylate with Styrene as an Unsaturated Organic Reagent To a mixture of glycopyrrolate bromide pure threo isomer (5 g, 0.013 mole), styrene (1.60 g, 0.015 mole), cyclohexane (23 ml) and p-toluene sulfonic acid monohydrate (2.38 g, 0.013 mole), 0.5 g (0.008 mole) of 42% hydrogen peroxide was added slowly at temperature 25-30° C. The obtained clear solution was stirred at 25-30° C. for 12 h and precipitation was observed. The solid was isolated by filtration to obtain 5.5 g material with un-reacted glycopyrrolate bromide content of 0.81%. The solid was dissolved in water (20 ml) at 50-55° C., cooled to 0-5° C., and then isolated by filtration and dried atmospherically to give 4 g (0.008 mole), with purity by HPLC 99.84%. yield 63.49%.

Example 4. Preparation of Glycopyrrolate Tosylate with 30% Hydrogen Peroxide

To a mixture of glycopyrrolate bromide pure threo isomer (5 g, 0.013 mole), cyclohexene (1.27 g, 0.015 mole), cyclohexane (23 ml) and p-toluene sulfonic acid monohydrate (2.38 g, 0.013 mole), 0.66 ml (0.00764 mole) of 30% hydrogen peroxide was added slowly at temperature 25-30° C. The obtained clear solution was stirred at 25-30° C. for 48 h and precipitation was observed. The solid was isolated by filtration to obtain 5 g material with un-reacted glycopyrrolate bromide content of 1.35%. The solid was dissolved in water (20 ml) at 50-55° C., cooled to 0-5° C., and isolated by filtration to give 4.2 g (0.008 mole), which were further dried atmospherically with purity by HPLC 99.77% and yield –66.66%.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A process for the preparation of glycopyrrolate tosylate comprising the step of reacting a halogen salt of glycopyrrolate with tosylic acid or a salt thereof in the presence of hydrogen peroxide and at least one unsaturated organic agent.

2. The process according to claim 1, wherein said process is performed in the presence of a mixture of at least one saturated organic agent and at least one unsaturated organic agent.

3. The process according to claim 1, wherein said at least one unsaturated organic agent is selected from cyclopentene, butene, pentene, cyclohexene, styrene, phenol and any combinations thereof.

4. The process according to claim 2, wherein said at least one saturated organic agent is selected from cyclohexane, n-hexane, dichloromethane, heptane, and any combinations thereof.

5. The process according to claim 1, wherein said halogen salt of glycopyrrolate is mixed with said at least one unsaturated organic agent prior to addition of said hydrogen peroxide.

6. The process according to claim 1, wherein said halogen salt of glycopyrrolate is mixed with said tosylic acid or salt thereof prior to addition of said hydrogen peroxide.

7. The process according to claim 1, wherein said halogen salt of glycopyrrolate is mixed with said tosylic acid or salt thereof and said at least one unsaturated organic agent prior to addition of said hydrogen peroxide.

8. The process according to claim 1, wherein said halogen salt of glycopyrrolate is mixed with said at least one unsaturated organic agent prior to reacting with said tosylic acid or salt thereof.

9. The process according to claim 1, wherein said hydrogen peroxide is added prior to or during said reaction of said halogen salt of glycopyrrolate and said tosylic acid or salt thereof.

10. The process according to claim 1, wherein said halogen salt of glycopyrrolate is a bromide salt thereof.

11. The process according to claim 1, wherein said tosylic acid or a salt thereof is p-toluene sulfonic acid monohydrate.

12. The process according to claim 1, providing a product having less than 2% halide content.

13. The process according to claim 1, providing a product having less than 1% halide content.

14. The process according to claim 1, providing a product having less than 0.5% halide content.

* * * * *